(12) United States Patent
Katoh et al.

(10) Patent No.: US 7,977,073 B2
(45) Date of Patent: Jul. 12, 2011

(54) POLYNUCLEOTIDE ENCODING A THERMOSTABLE AMIDE HYDROLASE AND METHODS FOR PRODUCING AN L-α-AMINO ACID

(75) Inventors: Osamu Katoh, Kanagawa (JP);
Takanori Akiyama, Kanagawa (JP);
Tetsuji Nakamura, Kanagawa (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 2235 days.

(21) Appl. No.: 10/487,240

(22) PCT Filed: Aug. 28, 2002

(86) PCT No.: PCT/JP02/08654
§ 371 (c)(1),
(2), (4) Date: Feb. 27, 2004

(87) PCT Pub. No.: WO03/020929
PCT Pub. Date: Mar. 13, 2003

(65) Prior Publication Data
US 2009/0215132 A1 Aug. 27, 2009

(30) Foreign Application Priority Data

Aug. 28, 2001 (JP) ................................. 2001-257736

(51) Int. Cl.
*C12P 13/04* (2006.01)
*C12P 21/06* (2006.01)
*C12N 15/00* (2006.01)
*C12N 1/20* (2006.01)
*C07H 21/04* (2006.01)

(52) U.S. Cl. .................. 435/106; 435/320.1; 435/252.3; 435/69.1; 435/252.1; 536/23.2; 536/23.7

(58) Field of Classification Search ........................ None
See application file for complete search history.

(56) References Cited

U.S. PATENT DOCUMENTS 5,766,918 A 6/1998 Petre et al.
6,057,491 A * 5/2000 Cigan et al. ................... 800/279

FOREIGN PATENT DOCUMENTS

WO 97/48794 12/1997
WO 00/63354 10/2000

OTHER PUBLICATIONS

Logan et al., J. Biol. Chem. 275:30019-30028, 2000.*
Nancy J. Fernald, et al., "Purification and Properties of Dicarboxylate ω-Amidase from *Bacillus subtilis* 168 and *Thermus aquaticus* YT-1 [1]", Archives of Biochemistry and Biophysics, vol. 153, No. 1, 1972, pp. 95-104.
Tae Kyou Cheong, et al., "Cloning of a Wide-Spectrum Amidase from *Bacillus stearothermophilus* RB388 in *Escherichia coli* and Marked Enhancement of Amidase Expression Using Directed Evolution", Enzyme and Microbial Technology, vol. 26, No. 2-4, XP-002304495, Feb. 2000, pp. 152-158.
W. J. J. Van Den Tweel, et al., "*Ochrobactrum anthropi* NCIMB 40321: a New Biocatalyst With Broad-Spectrum L-Specific Amidase Activity", Appl Microbial Biotechnol, vol. 39, No. 3, XP-008006772, 1993, pp. 296-300.

* cited by examiner

*Primary Examiner* — David J Steadman
(74) *Attorney, Agent, or Firm* — Oblon, Spivak, McClelland, Maier & Neustadt, L.L.P.

(57) ABSTRACT

The present invention relates to an amide hydrolase which is with excellent thermostability and stereoselectively hydrolyzes an α-amino acid amide; a gene encoding the enzyme protein; a novel recombinant vector containing the gene; a transformant containing the recombinant vector; and a process for producing an L-α-amino acid using the transformant.

19 Claims, 4 Drawing Sheets ically active L-α-amino acid by contacting a microorganism or a microbial enzyme with an α-amino acid amide are known (JP Patent Publication (Kokai) Nos. 59-159789 (1984), 61-119199 (1986), 62-55097 (1987), 1-277499 (1989) and 5-30992 (1993)). Each of these methods uses a reaction mediated by a microbial amide hydrolase. The amide hydrolase, also called amidase, catalyzes the hydrolysis reaction of an acid amide group into a carboxylic acid and an amine or ammonia. The microbial amide hydrolase is characterized in that it stereoselectively hydrolyzes an α-amino acid amide to produce an optically active L-α-amino acid. The term "optically active L-α-amino acid" refers to an amino acid containing a levorotatory enantiomer in a larger amount than the other enantiomer, or an amino acid consisting of a levorotatory enantiomer alone.

However, when a microorganism or microbial enzyme is industrially used for producing a substance; the stability and activity of the amide hydrolase used must be sufficiently high in view of cost performance. Since all microorganisms used in the aforementioned methods are mesophilic bacteria, which cannot proliferate at a temperature of 55° C. or higher, the amide hydrolases derived from these microorganisms are low in stability in the range of ordinary temperature or higher. Therefore, when a reaction takes place at high temperature, the problem that the reaction slows down or stops occurred because the enzyme becomes unstable.

DISCLOSURE OF THE INVENTION

An object of the present invention is to provide a process for efficiently producing an optically active L-α-amino acid by isolating a gene encoding an amide hydrolase with excellent thermostability and preparing a transformant by introducing the gene into an arbitrary host.

The present inventors conducted intensive studies. As a result, they isolated a gene encoding an amide hydrolase with excellent thermostability from a microorganism that can grow at 55° C. or higher. Furthermore, they successfully developed a technique capable of producing a biocatalyst with improved enzymatic activity by allowing multiple copies of the gene to be present in an arbitrary host by means of a genetic manipulation, thereby accomplishing the present invention.

More specifically, the present invention includes
(1) A protein of either (a) or (b):
  (a) a protein comprising an amino acid sequence represented by SEQ ID NO: 1; or
  (b) a protein comprising an amino acid sequence represented by SEQ ID NO: 1, wherein one or several amino acids have been deleted, replaced or added, and having amide hydrolase activity.

(2) An amide hydrolase gene encoding a protein of either (a) or (b):
  (a) a protein comprising an amino acid sequence represented by SEQ ID NO: 1; or
  (b) a protein comprising amino acid sequence represented by SEQ ID NO: 1, wherein one or several amino acids have been deleted, replaced or added, having amide hydrolase activity.

(3) A gene comprising DNA of either (a) or (b):
  (a) DNA consisting of a nucleotide sequence represented by SEQ ID NO: 2; or
  (b) DNA hybridizing with DNA consisting of a nucleotide sequence complementary to DNA consisting of the entire or part of a nucleotide sequence represented by SEQ ID NO: 2 under stringent conditions, and encoding a protein having amide hydrolase activity.

(4) A recombinant vector comprising the gene according to either (2) or (3).

(5) A transformant comprising the recombinant vector according to (4).

(6) A process for producing an amide hydrolase, comprising culturing the transformant according to (5) and recovering the protein of amino hydrolase from the cultured product.

(7) A process for producing an optically active L-α-amino acid, comprising culturing the transformant according to (5) and contacting the cultured product or a processed product thereof with an α-amino acid amide.

(8) A microorganism belonging to genus *Thermus* or genus *Bacillus*, capable of growing at 55° C. or higher, and producing an amide hydrolase with excellent thermostability.

(9) A process for producing an optically active L-α-amino acid, comprising culturing the microorganism according to (8) and contacting the cultured product or a processed product thereof with an α-amino acid amide.

The present specification incorporates the contents described in the specification and/or the drawings of Japanese Patent Application No. 2001-257736, on which the priority of the present application is based.

The present invention will be described in detail below.

1. Production of Optically Active L-α-amino Acid by Naturally Occurring Thermophilic Bacteria The present inventors found that an optically active L-α-amino acid can be efficiently produced by culturing a microorganism capable of growing at a temperature of 55° C. or higher and producing an amide hydrolase with excellent thermostability and contacting the resultant cultured product or a processed product thereof with an α-amino acid amide.

The amide hydrolase mediating the reaction is derived from a microorganism belonging to thermophilic bacteria capable of growing at a temperature of 55° C. or higher. The amide hydrolase is not particularly restricted as long as it has an ability to stereoselectively hydrolyze an α-amino acid amide to produce an optically active L-α-amino acid. Such an enzyme can be widely found in strains isolated from the nature or obtained from the Type Culture Collection. Examples include, for example, bacteria belonging to genus *Bacillus* and genus *Thermus*, more specifically, *Bacillus stearothermophilus* (NCIMB8923) and *Thermus aquaticus* (NCIMB 11243). These strains can be easily obtained from The National Collections of Industrial and Marine Bacteria (NCIMB).

The amide hydrolase of the present invention has an ability to stereoselectively hydrolyze an α-amino acid amide to produce an L-α-amino acid. As an enzyme having such an ability, amidases and amino peptidases are known.

Any medium may be used for culturing the aforementioned microorganism, as long as these microorganisms can be grown in the medium. As a carbon source, for example, saccharides such as glucose, sucrose, and maltose; organic acids such as acetic acid and citric acid or salts thereof; and alcohols such as ethanol and glycerol may be used. As a nitrogen source, for example, conventional naturally occurring nitrogen sources such as peptone, meat extract, yeast extract, and amino acids; and ammonium salts of inorganic and organic acids may be used. Besides these, inorganic salts, trace metal salts, and vitamins may be appropriately added as needed.

The aforementioned microorganisms may be cultured in accordance with a conventional method. For example, they may be cultured at pH 4 to 10, preferably pH 5 to 9, in the temperature range of 20 to 80° C., preferably 50 to 70° C., for 1 to 100 hours.

In the present invention, a cultured product obtained by culturing each of the microorganisms in a medium may be used directly, or bacterial cells obtained from the cultured product by a cell-collecting procedure such as centrifugation, the supernatant or a processed product thereof may be used. Examples of the processed product include bacterial homogenates, crude enzyme and purified enzyme prepared from the bacterial homogenates and the culture supernatant. Alternatively, bacterial cells, the processed products, and enzymes fixed to a carrier by a conventional method may be used.

Amide hydrolysis reaction is generally carried out by mixing an amino acid amide with an aqueous medium/an enzyme source to a concentration of 0.5 to 50% (the reaction substrate solution may be slurry). The addition amounts of cultured product, bacterial cells, or processed bacterial cells as an enzyme source are not particularly restricted, however, usually fall within the range of 0.01 to 10% in terms of dried cell mass. The reaction is generally carried out at 0 to 80° C., preferably, 20 to 70° C., in the range of pH 4 to 11, preferably, pH 6 to 10.

The L-α-amino acid thus produced and accumulated in the reaction solution is obtained by separation and purification carried out by combining known methods such as ion exchange and crystallization.

In the present invention, the term "amino acid amide" refers to a compound having a structure of an amino acid molecule in which carboxylic group has been replaced with acid amide and being represented by Formula I:

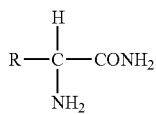

where R is a linear or branched alkyl group having 1 to 4 carbon atoms, a phenyl group, or halogen. The alkyl group or phenyl group may be substituted with at least one substituent selected from the group consisting of a mercapto group, hydroxyl group, amino group, carboxyl group, phenyl group, indolyl group, methylthio group, carbamoyl group, and imidazolyl group. Alternatively, R may be bound to an $NH_2$ group to form a ring. Specific examples of an α-amino acid amide may include phenylalanine amide, tryptophane amide, leucine amide, tert-leucine amide, valine amide, methionine amide, serine amide, histidine amide, and proline amide.

Specific examples of the L-α-amino acid to be produced in the present invention may include L-phenylalanine, L-tryptophane, L-leucine, L-tert-leucine, L-valine, L-methionine, L-serine, L-histidine, and L-proline. Furthermore, the optical purity of the amino acid amide to be used in the reaction is not particularly restricted.

2. Cloning of Amide Hydrolase Gene

The present inventors have further isolated *Thermus* sp. strain 0-3-1 (hereinafter referred to as "strain 0-3-1") among microorganisms capable of growing at 55° C. or higher, and producing an amide hydrolase with excellent thermostability, from hot-spring water of Gifu prefecture, and then an amide hydrolase protein and a gene encoding the protein are isolated from this strain. This strain has been deposited under the Budapest Treaty at an independent administrative incorporation, the Patent Organism Depositary Center of the National Institute of Advanced Industrial Science and Technology (Central 6, 1-1-1 Higashi, Tsukuba, Ibaraki, Japan) under the accession number FERM BP-8139 as of Aug. 5, 2002. The bacteriological characteristics of strain 0-3-1 are shown below:

| | |
|---|---|
| Morphology | Rod (0.5 × 2 μm), sometimes, chain-form or extended form |
| Gram staining | − |
| Spore | − |
| Motility | − |
| Colony morphology | Circular, peripheral flagellum distribution, slightly convex, glazed, milky white |
| Range of growth | |
| 80° C. | − |
| 70° C. | + |
| 55° C. | + |
| 40° C. | + (weak) |
| 30° C. | − |
| Reaction to oxygen | |
| Growth in anaerobic state | − |
| Catalase | + |
| Oxidase | + |
| O/F test | − |
| Acid production from carbohydrate | |
| Glycerol | − |
| Erythritol | − |
| D-arabinose | ± |
| L-arabinose | − |
| Ribose | + |
| D-xylose | − |
| L-xylose | − |
| Adonitol | − |
| β-methyl-D-xylose | − |
| Galactose | − |
| Glucose | − |
| Fructose | − |
| Mannose | − |
| Sorbose | − |
| Ramnose | − |
| Dulcitol | − |
| Inositol | − |
| Mannitol | − |
| Sorbitol | − |
| α-methyl-D-mannose | − |
| α-methyl-D-glucose | − |
| N-acetyl glucosamine | − |
| Amygdalin | − |
| Arbutin | − |
| Esculin | + |
| Salicin | − |
| Cellobiose | − |
| Maltose | − |
| Lactose | − |
| Melibiose | − |
| White sugar | − |
| Trehalose | − |
| Inulin | − |
| Melezitose | − |
| Raffinose | − |
| Starch | − |

-continued

| | |
|---|---|
| Glycogen | − |
| Xylitol | − |
| Gentiobiose | − |
| D-turanose | − |
| D-lyxose | − |
| D-tagatose | − |
| D-fucose | − |
| L-fucose | − |
| D-arabitol | − |
| L-arabitol | − |
| Gluconate | − |
| 2-Keto-gluconic acid | − |
| 5-Keto-gluconic acid | + |
| Characteristics of culture | |
| Bouillon liquid culture | film formed |
| Litmus milk | no change |
| Physiological characteristics | |
| Reduction of a nitrate | + |
| Denitrification reaction | − |
| MR test | − |
| VP test | − |
| Production of indole | − |
| Production of hydrogen sulfide | − |
| Hydrolysis of starch | + |
| Utilization of citric acid | |
| Koser | − |
| Christensen | − |
| Utilization of inorganic nitrogen source | |
| $NaNO_3$ | − |
| $(NH_4)_2SO_4$ | − |
| Urease | − |
| Hydrolysis | |
| Hide powder (Azure) | − |
| Elastin | − |
| Casein | − |
| DNase | + |
| α-galactosidase | − |
| β-galactosidase | + |
| Utilization of carbon sources | |
| Sodium acetate | − |
| Sodium glutamate | − |
| Sodium succinate | − |
| Sodium pyruvate | − |
| Proline | − |

(1) Culturing of Strain 0-3-1

As a culture medium composition for culturing strain 0-3-1, any composition may be employed as long as these microorganisms can grow in the medium. As a carbon source, for example, saccharides such as glucose, sucrose, and maltose; organic acids such as acetic acid and citric acid or salts thereof; and alcohols such as ethanol and glycerol may be used. As a nitrogen source, for example, conventional naturally occurring nitrogen sources such as peptone, meat extract, yeast extract, and amino acids; and ammonium salts of inorganic and organic acids may be used. Besides these, inorganic salts, trace metal salts, and vitamins may be appropriately added as needed. Strain 0-3-1 may be cultured in accordance with a conventional method. The cultivation may be carried out, for example, at pH 4 to 10, preferably pH 5 to 9, in a temperature range of 20 to 80° C., preferably 50 to 70° C., for 1 to 100 hours, using an aerobic or anaerobic incubator.

(2) Preparation of Chromosomal DNA

Chromosomal DNA is prepared by separation from strain 0-3-1. The separation and preparation of chromosomal DNA is carried out by any known method. For example, the method of Saito and Miura (Biochem. Biophys. Acta., 72, 619 (1963)) may be employed.

(3) Preparation of DNA Library

The chromosomal DNA of strain 0-3-1 obtained in the step (2) is partially digested with appropriate restriction enzymes (e.g., EcoRI, BamHI, Hind III, Sau3AI, MboI, and PstI). The resultant DNA is cleaved with restriction enzymes (e.g., BamHI and BglII), treated with alkaline phosphatase and ligated with a dephosphorylated vector to prepare a library. The vector to be used herein is not particularly restricted as long as it can replicate in a host cell. Examples of plasmid DNA include, for example, phage DNA, and cosmid DNA. Examples of a plasmid DNA include, for example, pBR322, pSC101, pUC18, pUC19, pUC118, pUC119, pACYC117, and pBluescript II SK (+). Examples of a phage DNA include, for example, λgt10, Charon 4A, EMBL-, M13mp18, and M13mp19. In the case where *Escherichia coli* (*E. coli*) is used as a host, pBR322, pUC118, pUC18, and pBluescript II SK (+), which have an autonomously replicating region in *E. coli*, may be used.

(4) Preparation of Transformant

A DNA fragment is ligated with a vector fragment by using a known DNA ligase. After the DNA fragment and the vector fragment are annealed, they are ligated to prepare a recombinant vector. The host to be transformed is not particularly restricted. Examples of *E. coli* strain include *E. coli* strains DH1, HB101, C600, MV1184, TH2, K12, JM109, and XL1-Blue. A recombinant vector is introduced into a host by a known method. When *E. coli*, for example, is used as a host, a calcium chloride method (Journal of Molecular Biology, 53, 154 (1970)) and an electroporation method (Current Protocols in Molecular Biology, 1, 184 (1994)) may be employed. In the case of a phage, an in-vitro packaging method (Current Protocols in Molecular Biology, 1, 571 (1994)) may be employed.

(5) Selection of Recombinant DNA Containing Amide Hydrolase Gene

The transformant obtained in the step (4) is inoculated onto an agar medium containing an α-amino acid amide as a sole nitrogen source. As an α-amino acid amide, one represented by Formula I may be used. A large colony formed on the agar medium is selected and then liquid cultivation is carried out using an appropriate medium. A medium for cultivation is not particularly restricted, however, when *E. coli* is used as a transformant host, a medium supplemented with at least one of nitrogen sources such as yeast extract, tryptone, polypeptone, corn steep liquor, and extract solutions of soy beans and wheat bran; at least one of inorganic salts such as sodium chloride, potassium dihydrogenphosphate, dipotassium phosphate, magnesium sulfate, magnesium chloride, ferric chloride, ferric sulfate, and manganese sulfate; and optionally a saccharine material and a vitamin, may be used. Furthermore, if necessary, an antibiotic for stabilizing a vector DNA and an inducer for expressing a gene may be added. Note that the initial pH of the medium is suitably adjusted at 7 to 9. The cultivation is preferably carried out at 25 to 42° C. for 6 to 24 hours by means of aeration submerged cultivation with stirring, shaking cultivation, or stationary cultivation. Bacterial cells are collected from the resultant cultured product, for example, by centrifugation and suspended in an appropriate buffer. The bacterial cell suspension is further suspended in a buffer containing an α-amino acid amide (e.g., DL-tert-leucine amide) to carry out a reaction. After a predetermined time, the yield of the corresponding α-amino acid is quantified by an analytical means such as high performance liquid chromatography. The transformant producing the α-amino acid is selected as a candidate strain possibly containing an amide hydrolase gene.

(6) Preparation of Restriction Map and Sub-Cloning

A plasmid is prepared from the transformant screened in the step (5) in accordance with a conventional method. The obtained plasmid is cleaved with restriction enzymes and electrophoretically analyzed. Based on the electrophoresis pattern, a restriction map is prepared. If necessary, a subclone having a shorter fragment is prepared.

(7) Confirmation of Amide Hydrolase Activity of Subclone

After a transformant is prepared with respect to the subclone obtained in the step (6), it is subjected to the cultivation and reaction procedure carried out in the step (5). It is determined whether a plasmid contains an amide hydrolase gene based on the presence or absence of α-amino acid production.

(8) Determination of Nucleotide Sequence and Identification of Amide Hydrolase Gene From the obtained subclones, a transformant having a short fragment inserted and having amide hydrolase activity is chosen and a plasmid is prepared. The inserted fragment in the plasmid is determined with respect to the nucleotide sequence. The nucleotide sequence is determined by a known method, e.g., the dideoxy method or the Maxam-Gilbert method using a fluorescent or radioactive marker. An open reading frame is searched in the nucleotide sequence thus determined and appropriately compared to known nucleotide sequences and amino acid sequences in a database.

The amino acid sequence of the amide hydrolase according to the present invention is represented by SEQ ID NO: 1, and the nucleotide sequence of its gene, by SEQ ID NO: 2. As long as a protein containing the amino acid sequence has amide hydrolase activity, it may have mutation caused by deletion, replacement, and addition of one or several amino acids in the amino acid sequence.

For example, one, or preferably 10 to 20, more preferably 5 to 10 amino acids may be deleted from the amino acid sequence represented by SEQ ID NO: 1; one, or preferably 10 to 20, more preferably 5 to 10 amino acids may be added to the amino acid sequence represented by SEQ ID NO: 1; or one, or preferably 10 to 20, more preferably 5 to 10 amino acids of the amino acid sequence represented by SEQ ID NO: 1 may be replaced with other amino acids. Furthermore, the gene of the present invention may include a gene hybridizing, under stringent conditions, with a sequence that is complementary to the DNA consisting of all or part of the nucleotide sequence of the amide hydrolase gene of the present invention, and encoding a protein with amide hydrolase activity. The term "stringent conditions" refers to those in which a specific hybrid is formed and a nonspecific hybrid is not formed. In other words, the conditions in which DNA having a high homology (not less than 90%, preferably, 95% or more of homology) to the amide hydrolase gene of the present invention can be hybridized. More specifically, such conditions can be attained by performing hybridization in the presence of 0.5 to 1 M NaCl, at 42 to 68° C.; in the presence of 50% formaldehyde, at 42° C.; or in an aqueous solution, at 65 to 68° C., followed by washing a filter with a 0.1 to 2×SSC (saline sodium citrate) solution, at room temperature to 68° C.

The term "part of the sequence" refers to a nucleotide sequence of DNA containing part of the nucleotide sequence of the amide hydrolase gene, provided that the DNA encodes a protein having an amide hydrolase activity. Furthermore, the term "part of the sequence" refers to DNA having a sufficient length of a nucleotide sequence to hybridize under the stringent conditions, for example, a nucleotide sequence of at least 10 bases, preferably at least 50 bases, more preferably at least 200 bases.

A mutation of a gene may be introduced in accordance with a known method such as the Kunkel method, the Gapped duplex method, or the like, by using, for example, a mutation introduction kit according to a site-specific mutation induction method, such as Mutan-K (manufactured by TAKARA), Mutan-G (manufactured by TAKARA), or a kit of an LA PCR in vitro Mutagenesis series (manufactured by TAKARA). Note that after the nucleotide sequence is determined by the method mentioned above, the gene of the present invention can be obtained by chemical synthesis, a PCR method using a chromosomal DNA as a template, or hybridization using a DNA fragment having the nucleotide sequence as a probe.

3. Preparation of Recombinant Vector and Transformant

A recombinant vector of the present invention can be obtained by ligating a gene of the present invention or a part thereof to an appropriate vector. Furthermore, a transformant of the present invention can be obtained by introducing the recombinant vector of the present invention into a host such that the gene of the present invention can be expressed therein. The term "part" refers to a portion of an amide hydrolase gene that is to be introduced into a host and can express the amide hydrolase of the present invention.

The vector to which the gene of the present invention is inserted is not particularly restricted as long as it can replicate in host cells. Examples of a plasmid DNA include, for example, phage DNA, and cosmid DNA. Examples of a plasmid DNA include, for example, pBR322, pSC101, pUC18, pUC19, pUC118, pUC119, pACYC117, and pBluescript II SK (+). Examples of a phage DNA include, for example, λgt10, Charon 4A, EMBL-, M13mp18, and M13mp19.

A host is not particularly restricted as long as it can express a desired gene. Examples thereof include, for example, bacteria belonging to genus *Ralstonia* such as *Ralstonia eutropha*; bacteria belonging to genus *Pseudomanas* such as *Pseudomonas putida*; bacteria belonging to genus *Bacillus* such as *Bacillus subtilis*; bacteria belonging to genus *Escherichia* such as *Escherichia coli*; a yeast belonging to genus *Saccharomyces* such as *Saccharomyces cerevisiae*; yeasts belonging to genus *Candida* such as *Candida maltosa*; animal cells such as COS cells, CHO cells, mouse L cells, rat GH3, and human FL cells; and insect cells such as SF9 cells.

When bacteria such as *E. coli* is used as a host, it is preferable that a recombinant vector of the present invention is self-replicable in the host and contains a promoter, DNA of the present invention, and a transcription termination sequence. Examples of an expression vector include vectors which can be replicated and retained in a wide variety of hosts, such as pLA2917 (ATCC 37355) having an RK2 replication origin and pJRD215 (ATCC 37533) having an RSF1010 replication origin.

As a promoter, any promoter may be used as long as it can express in a host. For example, promoters derived from *E. coli* and phages, such as a trp promoter, lac promoter, $P_L$ promoter, $P_R$ promoter, T7 promoter may be used. A method of introducing a recombinant vector into bacteria is not particularly restricted, however, for example, a method using calcium ions (Current Protocols in Molecular Biology, 1, 181 (1994)) and an electroporation method may be employed.

When a yeast is used as a host, for example, an expression vector such as YEp13 or YCp50 may be used. Examples of a promoter include, for example, gal 1 promoter, gal 10 promoter, heat-shock protein promoter, and GAP promoter. A method of introducing a recombinant vector into a yeast is not particularly restricted, however, for example, an electroporation method, spheroplast method (Proc. Natl. Acad. Sci. USA, 84, 192, 9-1933 (1978)), and a lithium acetate method (J. Bacteriol., 153, 163-168 (1983)) may be employed.

When animal cells are used as a host, expression vectors such as pcDNAI, pcDNAI/Amp (invitrogen Corporation)

may be used. Examples of a promoter include, for example, an SRx promoter, SV40 promoter, and CMV promoter. A method of introducing a recombinant vector into animal cells is not particularly restricted, however, for example, electroporation method, calcium phosphate method, and lipofection method may be employed.

4. Production of Amide Hydrolase

An amide hydrolase of the present invention is produced by culturing a transformant of the present invention in a medium, thereby producing and accumulating the amide hydrolase in the cultured product (cultured cells or the supernatant), and recovering amide hydrolase from the cultured product. The method of culturing a transformant of the present invention is carried out in accordance with a conventional method for culturing a host. Examples of a medium for culturing a transformant obtained by using bacteria such as *E. coli* as a host, include complete medium or synthetic medium, such as LB medium and M9 medium. Amide hydrolase is obtained by culturing bacterial cells under aerobic conditions in the range of 0 to 70° C. for 1 to 80 hours to accumulate and recover the amide hydrolase. The medium is maintained at about pH 7 during culturing. The adjustment of pH is carried out by using an inorganic acid, an organic acid, or an alkaline solution.

A carbon source is required for growing a microorganism and examples thereof include, for example, carbohydrates such as glucose, fructose, sucrose, and maltose. Examples of a nitrogen source include, for example, ammonium salts such as ammonia, ammonium chloride, ammonium sulfate, and ammonium phosphate, meat extract, yeast extract, and corn steep liquor. Examples of an inorganic substance include, for example, potassium dihydrogenphosphate, dipotassium phosphate, magnesium phosphate, magnesium sulfate, and sodium chloride.

During cultivation, antibiotics such as Kanamycin, Ampicillin, and Tetracycline may be added to a medium. When a microorganism transformed with an expression vector having an inducible promoter is cultured, an inducer may be added to a medium. For example, isopropyl-β-D-thio-galactopyranoside (IPTG), and indol acrylic acid (IAA) may be added to a medium.

As a medium for culturing a transformant obtained by using animal cells as a host, for example, RPMI-1640, DMEM medium, and these mediums having fetus bovine serum added thereto may be used. Cultivation may be generally carried out in the presence of 5% $CO_2$ at 30 to 40° C. for 1 to 7 days. During cultivation, an antibiotic such as Kanamycin or penicillin may be added to a medium. An amide hydrolase is purified by collecting the cultured product with centrifugation (cells are disrupted by a sonicator), and subjecting it to affinity chromatography, cation or anion exchange chromatography, or gel filtration singly or in combination. The purified substance is confirmed as a desired enzyme by a conventional method such as SDS polyacrylamide gel electrophoresis or Western blotting.

5. Production of Optically Active L-α-amino Acid Using Transformant or Processed Product Thereof Bacterial cells are collected from the cultured product of a transformant obtained above, for example, by centrifugation and suspended in an appropriate buffer. The bacterial cell suspension is further suspended in a buffer containing an α-amino acid amide to carry out a reaction. In this manner, an optically active L-α-amino acid can be produced. The reaction is carried out at a temperature of 0 to 80° C., preferably 10 to 70° C., for 0.1 to 100 hours, preferably, 0.5 to 80 hours, in the range of about pH 4 to 11.

The reaction may be carried out by using a processed cultured product. Examples of the processed product include, for example, bacteria disruptions, crude enzyme and purified enzyme prepared from the bacterial homogenate or the culture supernatant. Alternatively, bacterial cells, the processed products, enzymes fixed to a carrier in accordance with a conventional method and the like may be used.

The intracellular content and optical purity of the produced L-α-amino acid can be measured and analyzed by removing bacterial cells or enzymes, for example, by centrifugation and subjecting the supernatant to high performance liquid chromatography, NMR and the like.

It has been found that a transformant or amide hydrolase according to the present invention can maintain its amide hydrolase activity even at high temperature, and that by using them, optically active L-α-amino acid can be more effectively synthesized compared to a conventional case where a microorganism or a microbial enzyme is used.

BEST MODE FOR CARRYING OUT THE INVENTION

Figure 1:
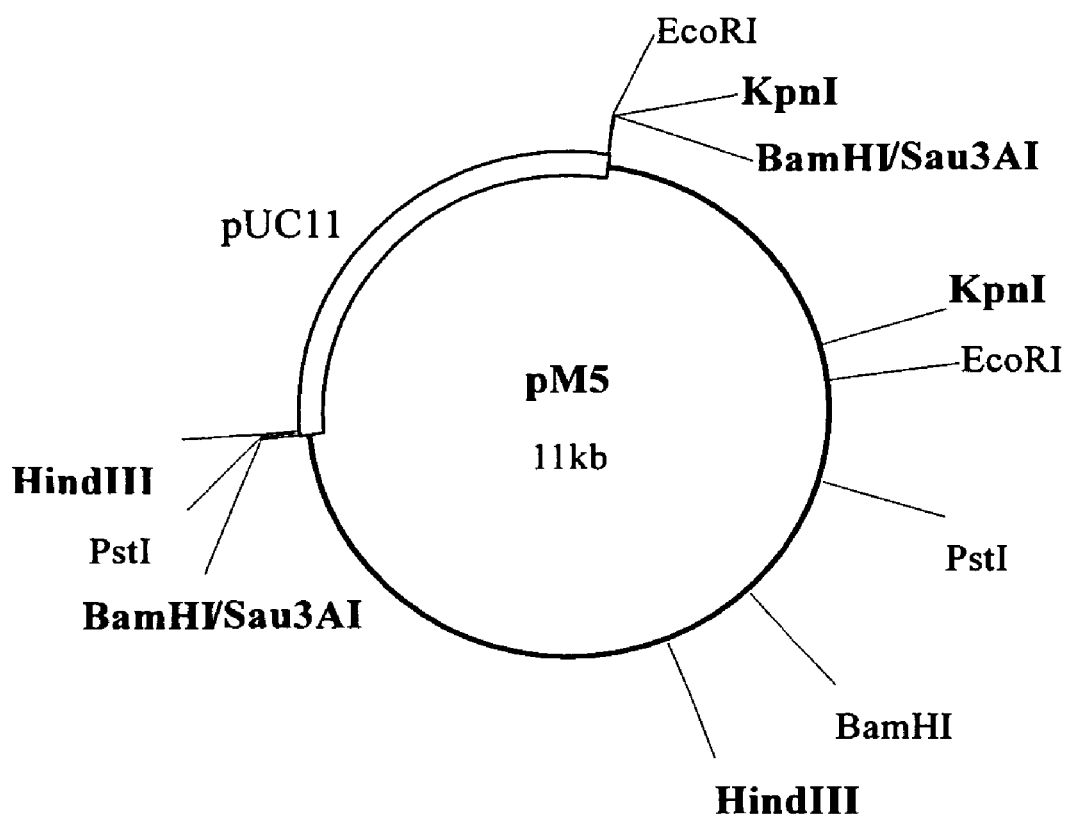
FIG. 1 is a restriction map of recombinant plasmid pM5.

The present invention will now be explained in more detail with reference to Examples, which should not be construed as limiting the technical scope of the present invention.

Example 1

First, 100 ml of medium (pH 7.5) containing 0.8% polypeptone, 0.4% yeast extract, 0.2% NaCl, 0.005% $CaCl_2.2H_2O$, and 0.008% $MgCl_2.6H_2O$ was placed in a 500 ml-Erlenmeyer flask and sterilized in an autoclave. To the medium, *Thermus aquaticus* NCIMB11243 was inoculated and cultured at 70° C. for 3 days.

After completion of the culturing, bacterial cells were centrifugally collected from the cultured product, washed once with 50 mM $NH_4Cl$—$NH_4OH$ buffer (pH 9.0) of the same amount as the cultured product and suspended in 5 ml of the same buffer.

To 1.5 ml of the bacterial cell suspension, 1.5 ml of a 2% phenylalanine amide solution was added and a reaction was carried out at 70° C. for one hour. After completion of the reaction, bacterial cells were centrifugally removed from the reaction solution. Thereafter, analysis of quantity and optical purity was carried out using high performance liquid chromatography.

As a result, L-phenylalanine (0.28%) was produced. Its optical purity was 100% ee.
[HPLC Analysis Condition]
(Quantification Analysis)
Column: Inertsil ODS-3V (4.64×250 mm)
Mobile phase: 0.1% aqueous solution of phosphoric acid: acetonitrile (80:20)
Flow rate: 1 ml/min
Detection: UV (254 nm)
(Optical Purity Analysis)
Column: SUMICHIRAL OA-5000 (4.6%×150 mm)
Mobile phase: 2 mM copper sulfate:methanol (70:30)

Flow rate: 1 min
Detection: UV (254 nm)

Example 2

First, 100 ml of medium (pH 7.3) containing 0.5% polypeptone, 0.3% meat extract, and 0.8% NaCl was placed in a 500 ml-Erlenmeyer flask and sterilized in an autoclave. To the medium, *Bacillus stearothermophilus* NCIMB8923 was inoculated and cultured at 55° C. for 3 days.

After completion of the cultivation, bacterial cells were centrifugally collected from the cultured product, washed once with 50 mM $NH_4Cl$—$NH_4OH$ buffer (pH 9.0) of the same amount as the cultured product and suspended in 5 ml of the same buffer.

To 1.5 ml of the bacterial cell suspension, 1.5 ml of a 2% phenylalanine amide solution was added and a reaction was carried out at 55° C. for one hour. After completion of the reaction, bacterial cells were centrifugally removed from the reaction solution. Thereafter, analysis was carried out using high performance liquid chromatography in the same conditions as in Example 1. As a result, L-phenylalanine (0.49%) was produced. The optical purity was 100% ee.

Example 3

To 1.5 ml of a bacterial cell suspension prepared in the same manner as in Example 1, 1.5 ml of a 2% tert-leucine amide solution was added and a reaction was carried out at 70° C. for 70 hours. After bacterial cells were centrifugally removed from the reaction solution, analysis was carried out by high performance liquid chromatography. As a result, L-tert-leucine (0.38%) was produced. The optical purity was 100% ee.

[HPLC Analysis Conditions]
(Quantification Analysis)
Column: Inertsil ODS-3V (4.6ϕ×250 mm)
Mobile phase: 0.1% aqueous solution of phosphoric acid
Flow rate: 1 ml/min
Detection: RI
(Optical Purity Analysis)
Column: SUMICHIRAL OA-5000 (4.6ϕ×150 mm)
Mobile phase: 2 mM copper sulfate:methanol (85:15)
Flow rate: 1 ml/min
Detection: UV (254 nm)

Example 4

To 1.5 ml of a bacterial cell suspension prepared in the same manner as in Example 2, 1.5 ml of a 2% tert-leucine amide solution was added and a reaction was carried out at 70° C. for 70 hours. After bacterial cells were centrifugally removed from the reaction solution, analysis was carried out by high performance liquid chromatography. As a result, L-tert-leucine (0.31%) was produced. The optical purity was 100% ee.

Example 5

(1) Cultivation of Strain 0-3-1

Strain 0-3-1 was inoculated onto 100 ml of nutrition medium (0.2% polypeptone, 0.1% yeast extract, 0.2% NaCl, 0.005% $CaCl_2.2H_2O$, 0.008% $MgCl_2.6H_2O$, pH7.5) and cultured at 70° C. for 3 days.

(2) Preparation of Chromosomal DNA

After completion of the culturing, bacterial cells were centrifugally collected and washed with sterilized distilled water, and thereafter, suspended in 2 ml of a saline-EDTA solution (0.1 M EDTA, 0.15 M NaCl). After 10 mg of Lysozyme was added and shaken at 37° C. for one hour, 10 ml of a Tris-SDS solution (1% SDS, 0.1 M NaCl, 0.1 M Tris, pH9.0) was added gently with shaking, and further proteinase K (manufactured by Merk) was added so as to make a final concentration of 1 mg. The resultant mixture was shaken at 37° C. for one hour. Subsequently, to the resultant solution, an equivalent amount of TE saturated phenol (TE: 10 mM Tris, 1 mM EDTA, pH8.0) was added, and resultant mixture was stirred, and centrifuged. After the upper phase was taken and two-fold amount of ethanol was added thereto, DNA was rolled up by a glass rod. Phenol was removed by adding 90%, 80%, and 70% ethanol successively. Subsequently, the DNA was dissolved in 5 ml of a TE buffer and a ribonuclease A solution (100° C., heat-treated for 15 minutes in advance) was added to the resultant solution so as to make a concentration of 10 mg/ml and shaken at 37° C. for 30 minutes. Further, proteinase K was added to make a final concentration of 1 mg and shaken at 37° C. for 30 minutes, and thereafter an equivalent amount of TE saturated phenol was added and centrifuged to separate into an upper phase and a lower phase, of which the upper phase was taken (hereinafter, this operation will be referred to as "phenol extraction"). After phenol extraction operation was repeated twice, the same amount of chloroform (containing 4% isoamyl alcohol) was added and thereafter the same extraction was repeated (hereinafter, this operation will be referred to as "chloroform extraction"). After that, two-fold amount of ethanol was added to the upper layer, DNA was recovered by rolling it up by a glass rod and dissolved in 1 ml of sterilized water to obtain a chromosomal DNA sample.

(3) Preparation of DNA Library

To 200 μl of chromosomal DNA of strain 0-3-1 obtained in the step (2), 40 μl of a 10-fold buffer for a restriction enzyme reaction, 160 μl of sterilized water, and 2 μl of restriction enzyme, Sau3AI, were added. The reaction mixture was incubated at 37° C. for 2 minutes and then subjected to ethanol precipitation, thereby recovering DNA. The obtained DNA was subjected to agarose-gel electrophoresis. A about 4 to 7 kb DNA fragment was cleaved out from the gel and recovered by a DNA PREP (manufactured by Diatron). The DNA fragment was inserted into an *E. coli* vector, pUC118, at a BamHI site by using DNA Ligation Kit Ver. I (manufactured by Takara Shuzo) to construct a recombinant DNA library. The pUC118 fragment used in ligation was prepared as follows. To 2 μl of a pUC118 preservation solution, 5 μl of a 10-fold buffer for a restriction enzyme, 40 μl of sterilized water, and 3 μl of restriction enzyme, BamHI, were added and a reaction was carried out at 37° C. for 2 hours. Thereafter, phenol extraction and chloroform extraction were carried out, fragments were precipitated with ethanol, dried and dissolved in 50 μl of sterilized water. Furthermore, 1 μl of alkaline phosphatase (manufactured by Takara Shuzo), 10 μl of a 10-fold buffer, and 39 μl of sterilized water were added, a reaction was carried out at 65° C., and subjected to phenol extraction and chloroform extraction. Thereafter, following ethanol precipitation, fragments were dried and dissolved in sterilized water.

(4) Preparation of Transformant

*E. coli* strain, JM109 was inoculated in 1 ml of LBAmp medium (1% Bacto triptone, 0.5% Bacto yeast extract, 0.5% NaCl, 0.01% Ampicilline) and aerobically preincubated at 37° C. for 5 hours. Then, 0.4 ml of the resultant cultured product was added to 40 ml of SOB medium (2% Bacto triptone, 0.5% Bacto yeast extract, 10 mM NaCl, 2.5 mM KCl, 1 mM $MgSO_4$, 1 mM $MgCl_2$) and the medium was cultured at 18° C. for 20 hours. After the cultured product was centrifuged to collect bacterial cells, 13 ml of a cold TF solution (20 mM PIPES-KOH (pH6.0), 200 mM KCL, 10 mM $CaCl_2$, 40 mM $MnCl_2$) was added to the bacterial cells, allowed to stand at 0° C. for 10 minutes and again centrifuged to remove the supernatant. The precipitated *E. coli* cells were suspended in 3.2 ml of the cold TF solution and 0.22 ml of dimethylsulfoxide was added and allowed to stand at 0° C. for 10 minutes. To 200 μl of the competent cells thus prepared, 10 μl of the solution containing a recombinant plasmid (DNA library) prepared in the step (3) was added. The resultant solution was allowed to stand at 0° C. for 30 minutes, and then heat shock was given to the solution at 42° C., for 30 seconds. After the solution was cooled at 0° C. for 2 minutes, 1 ml of SOC medium (20 mM glucose, 2% Bacto triptone, 0.5% Bacto yeast extract, 10 mM NaCl, 2.5 mM KCl, 1 mM $MgSO_4$, 1 mM $MgCl_2$) was added to the solution, and shaking cultivation was carried out at 37° C. for one hour. 200 μl of the cultured product was seeded in each LBAmp agar medium (LBAmp medium containing 1.5% agar) and cultured at 37° C. overnight to obtain transformants.

(5) Selection of Recombinant DNA Containing Amide Hydrolase Gene

The transformant colony obtained in the step (4) was inoculated onto an agar medium containing lactamide. The agar medium containing lactamide was prepared by applying 100 μl/plate of a 20% DL lactamide solution previously sterilized by a filter onto the agar medium (0.2% glycerol, 0.05% NaCl, 0.002% thiamine hydrochloride, 0.6% $Na_2HPO_4$, 0.3% $KH_2PO_4$, 0.001% $ZnSO_4.7H_2O$, 0.0025% $MgSO_4.7H_2O$, 0.001% $MnSO_4.4-6H_2O$, 0.0001% $CaCl_2.2H_2O$, 1.5% agar) which was previously placed and solidified in a sterilized Petri dish in an amount of 20 ml per dish. After cultivation is carried out at 37° C. for 3 days, colonies were formed. Of them, 12 large colonies were inoculated in 1.5 ml of LBAmp medium containing 1 mM IPTG and cultured at 37° C. overnight. After cultivation, the bacterial cells are centrifugally collected and washed with a 50 mM $NH_4Cl$—$NH_4OH$ (pH 9.0) buffer and suspended in 0.7 ml of the same buffer. Subsequently, 0.5 ml of the bacterial cell suspension was pretreated at 70° C. for 5 to 10 minutes, mixed with 0.5 ml of a 50 mM $NH_4Cl$—NHOH buffer (pH 9.0) containing 2% DL-tert-leucine amide and incubated at 70° C. for 24 hours. After incubation, bacterial cells were centrifugally removed and analyzed by high performance liquid chromatography. The analysis conditions are shown below.
(Quantification Analysis)
Column: Inertsil ODS-3V (4.6φ×250 mm)
Mobile phase: 0.1% aqueous solution of phosphoric acid: acetonitrile (80:20)
Flow rate: 1 ml/min
Detection: UV (254 nm)
(Optical Purity Analysis)
Column: SUMICHIRAL OA-5000 (4.6φ×150 mm)
Mobile phase: 2 mM copper sulfate:methanol (70:30)
Flow rate: 1 ml/min
Detection: UV (254 nm)

As a result, it was observed that L-tert-leucine (0.47 to 0.63%) was produced in 5 clones. The optical purity of each clone was 100% ee.

(6) Preparation of Restriction Map and Subcloning

Figure 2:
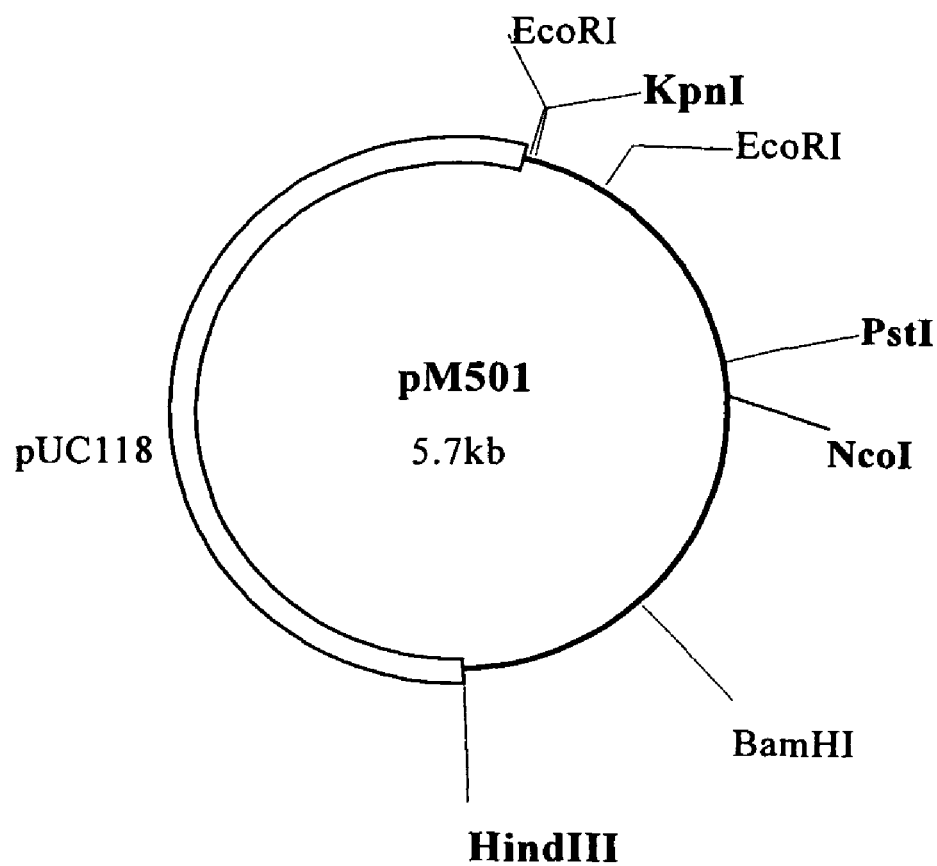
FIG. 2 is a restriction map of recombinant plasmid pM501.
Figure 3:
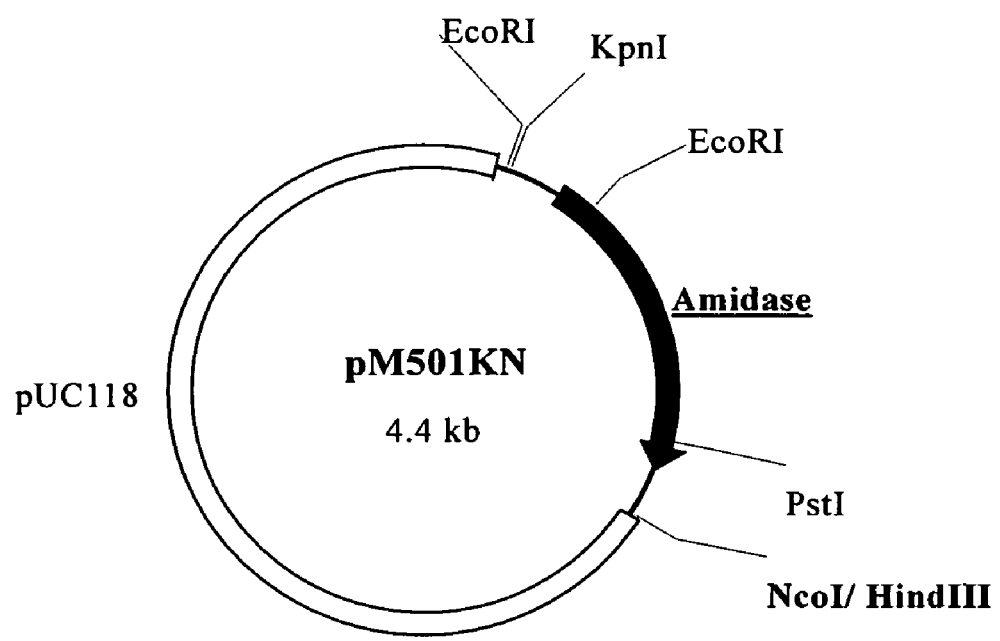
FIG. 3 is a restriction map of recombinant plasmid pM501KN.
Figure 4:
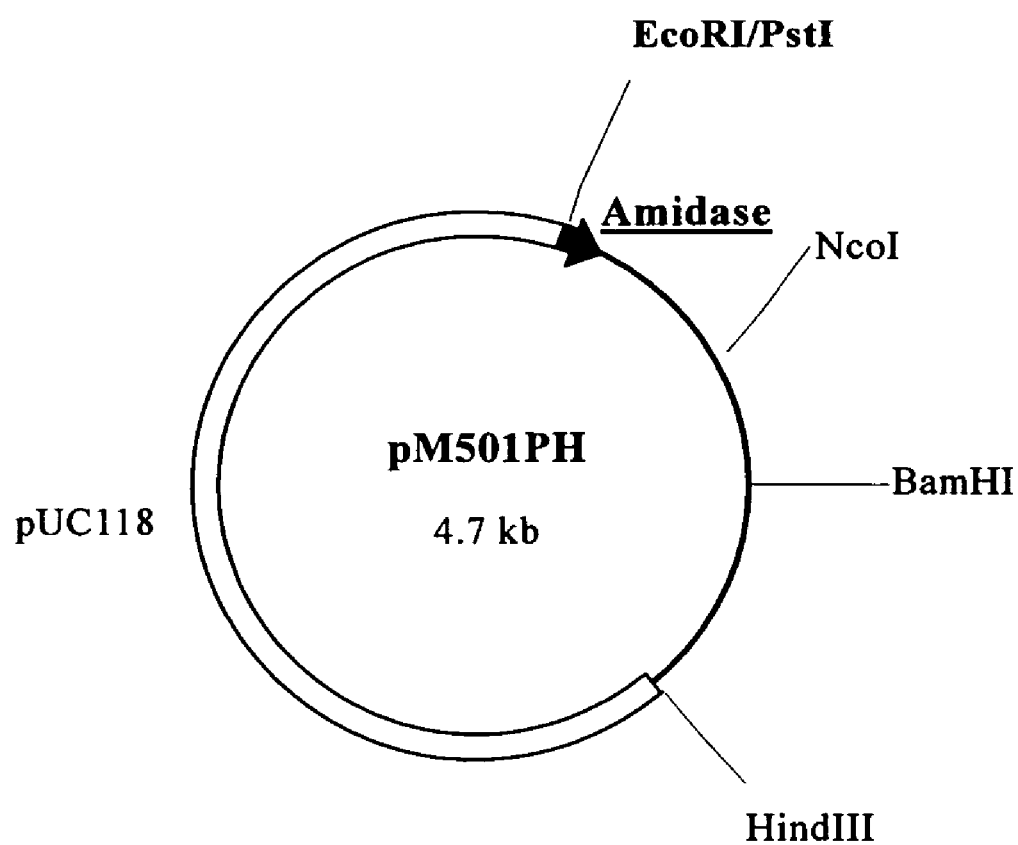
FIG. 4 is a restriction map of recombinant plasmid pM501PH.

Of five clones separated in the step (5), one was selected and designated as M5. From this clone, a plasmid was purified by FlexiPrep (manufactured by Amersham Bioscience). The obtained plasmid (pM5) was digested with restriction enzymes and analyzed by 0.7% agarose gel electrophoresis. As a result, the restriction map having an about a 8 kb fragment inserted therein was obtained as shown in FIG. 1. Subsequently, from the inserted fragment of pM5, an about 2 kb KpnI fragment and an about 3.5 kb Hind III fragment were removed and the remaining fragments were self-ligated to prepare a sub-clone pM501 (FIG. 2). Furthermore, subcloning was carried out by using an NcoI site and a PstI site of the inserted fragment. More specifically, pM501 was cleaved at an NcoI site and at a Hind III site in the C terminal of the inserted fragment, thereby removing an about 0.7 kb NcoI-HindIII fragment. After that, both cleaved ends were smoothened and self-ligated to produce pM501KN (FIG. 3). Furthermore, pM501KN was cleaved at a PstI site and an EcoRI site of multi-cloning site in the N-terminal of the inserted fragment, thereby removing an about 1 kb EcoRI-PstI fragment. After both cleaved ends were smoothened and self-ligated to prepare plasmid pM501PH (FIG. 4).

(7) Confirmation of Amide Hydrolase Activity of Subclone

Using plasmids pM501, pM501KN, and pM501PH prepared in the step (6) and a pM5 as a positive control, *E. coli* strain JM109 was transformed in accordance with the method described in the step (4). The obtained colonies of transformants (JM109/pM501, JM109/pM501KN, JM109/pM501PH, and JM109/pM5) were inoculated in 1.5 ml of 1 mM IPTG-containing LBAmp medium and cultured at 37° C. overnight. After culturing, bacterial cells are centrifugally collected, washed with a 50 mM $NH_4Cl$—$NH_4OH$ buffer (pH9.0) and suspended in 0.7 ml of the same buffer. After 0.5 ml of the bacterial cell suspension was pretreated at 70° C. for 5 to 10 minutes and mixed with 0.5 ml of a 50 mM $NH_4Cl$—$NH_4OH$ buffer (pH 9.0) containing 2% DL-tert-leucine amide, the resultant mixture was incubated at 70° C. for 30 minutes. After incubation, bacterial cells were centrifugally removed and analyzed by high performance liquid chromatography under the conditions described in the step (5). As a result, transformants JM109/pM501, JM109/pM501KN, and JM109/pM5 produced L-tert-leucine in a yield of 0.14%, 0.13%, and 0.14%, respectively; whereas, JM109/pM501PH did not produce L-tert-leucine, at all. Therefore, it was demonstrated that the desired amide hydrolase gene is present in an about 1.2 kb inserted fragment of pM501KN.

(8) Determination of Nucleotide Sequence

The nucleotide sequence of the KpnI-NcoI fragment (about 1.2 kb) in the inserted fragment of plasmid pM501KN obtained in the step (6) was determined in accordance with the dideoxy method by a fluorescence sequencer, ALF II (manufactured by Pharmacia). As a result, an open reading frame (SEQ ID NO: 2) encoding the amino acid sequence represented by SEQ ID NO: 1 was detected. An amino acid sequence having a homology with the amino acid sequence represented by SEQ ID NO: 1 was screened from known amino acid sequences in BLAST (blastp) of Japanese DNA databank. As a result, a putative protein (pirB90458) of *Sulfolobus fataricus* exhibited a 41% homology; putative acetoamide hydrolase (dadAP000981-165) of *Sulfolobus tokodaii*, a 42% homology; and a putative acetoamide hydrolase (dadAP000059-268) of *Aeropyrum pernix*, a 36% homology. However, each of them has a low homology. The function of the proteins showing homology are still unknown. The proteins do not have a function to stereospecifically hydrolyze α-amino acid amide. From the facts, the amide hydrolase of the present invention is considered as a novel amide hydrolase with an excellent stability.

Example 6

(1) Production of Optically Active L-α-amino Acid by Using *E. coli* JM109/pM501KN Optically active L-α-amino acid was produced by use of an *E. coli* transformant carrying pM501KN. More specifically, JM109/pM501KN was inoculated in 1.5 ml of LBAmp medium and cultured at 37° C. for 6 hours. The obtained cultured product was inoculated in 40 ml of 1 mM IPTG containing LBAmp medium and cultured with shaking at 37° C. for 17 hours. From the obtained cultured product, a 5 ml aliquot was taken and subjected to centrifugation to collect bacterial cells. The bacterial cells were washed with a 50 mM NCl—$NH_4OH$ buffer (pH 9.0) and suspended in 2 ml of the same buffer. After the cell suspension was treated with heat at 70° C. for 30 minutes, a 0.5 ml aliquot was taken, mixed with 0.5 ml of a 50 mM $NH_4Cl$—$NH_4OH$ buffer (pH 9.0) containing 2% DL-tert-leucine amide, and incubated at 70° C. for 3 hours. After incubation, bacterial cells were centrifugally removed and analyzed by high performance liquid chromatography under the conditions described in the step (5). As a result, L-tert-leucine (0.55%) was produced and its optical purity was 100% ee. Note that pM501KN has been deposited under the Budapest Treaty at an independent administrative incorporation, the Patent Organism Depositary center of the National Institute of Advanced Industrial Science and Technology (Central 6, 1-1-1 Higashi, Tsukuba, Ibaraki, Japan) under the accession number FERM BP-8138 as of Aug. 5, 2002.

All publications, patents and patent applications cited herein are incorporated by references in its entirety.

INDUSTRIAL APPLICABILITY

According to the present invention, a large number amide hydrolases with excellent thermostability can be present in a host by a gene recombination technology. Therefore, it is possible to provide a biocatalyst with greatly improved thermostability and activity compared to a conventional method. As a result, a method of industrially producing an optically active L-α-amino acid with high efficiency can be provided.

Sequence List (Free Text)
SEQ ID NO: 1: Peptide
SEQ ID NO: 2: DNA

The invention claimed is:

1. An isolated polynucleotide encoding a protein, wherein the protein comprises:
   (a) the amino acid sequence of SEQ ID NO: 1; or
   (b) the amino acid sequence of SEQ ID NO: 1, except that one to twenty amino acids have been deleted, replaced or added and which protein has amide hydrolase activity.

2. A recombinant vector comprising the isolated polynucleotide according to claim 1.

3. A transformant comprising the recombinant vector according to claim 2.

4. A process for producing an amide hydrolase, comprising:
   culturing the transformant according to claim 3, and
   recovering an amide hydrolase encoded by the recombinant vector from the cultured transformant.

5. A process for producing an optically active L-α-amino acid, comprising:
   culturing the transformant according to claim 3, and
   contacting the cultured transformant with an α-amino acid amide to produce an optically active L-α-amino acid.

6. An isolated polynucleotide, wherein the polynucleotide comprises:
   (a) the polynucleotide sequence of SEQ ID NO:2; or
   (b) a polynucleotide that is at least 95% homologous to the polynucleotide sequence of SEQ ID NO:2 and which encodes a protein having amide hydrolase activity.

7. A recombinant vector comprising the isolated polynucleotide according to claim 6.

8. A transformant comprising the recombinant vector according to claim 7.

9. A process for producing an amide hydrolase, comprising:
   culturing the transformant according to claim 8, and
   recovering an amide hydrolase encoded by the recombinant vector from the cultured transformant.

10. A process for producing an optically active L-α-amino acid, comprising:
    culturing the transformant according to claim 8, and
    contacting the cultured transformant with an α-amino acid amide to produce an optically active L-α-amino acid.

11. An isolated microorganism, wherein said microorganism is the strain deposited under accession number FERM BP-8139.

12. A process for producing an optically active L-α-amino acid, comprising:
    culturing the microorganism according to claim 11, and
    contacting the cultured microorganism with an α-amino acid amide to produce an optically active L-α-amino acid.

13. The isolated polynucleotide of claim 1, which encodes a protein comprising the amino acid sequence of SEQ ID NO: 1.

14. The isolated polynucleotide of claim 1, which encodes a protein comprising the amino acid sequence of SEQ ID NO: 1, except that one to twenty amino acids have been deleted, replaced or added and which has amide hydrolase activity.

15. The isolated polynucleotide of claim 6 consisting of the polynucleotide sequence of SEQ ID NO: 2.

16. The isolated polynucleotide of claim 6, which is at least 95% homologous to the polynucleotide sequence of SEQ ID NO: 2 and which encodes a protein having amide hydrolase activity.

17. A process for producing an optically active L-α-amino acid, comprising:
    culturing the transformant according to claim 3,
    recovering an amide hydrolase encoded by the recombinant vector from the cultured transformant, and
    contacting the recovered amide hydrolase with an α-amino acid amide to produce an optically active L-α-amino acid.

18. A process for producing an optically active L-α-amino acid, comprising:
    culturing the transformant according to claim 8,
    recovering an amide hydrolase encoded by the recombinant vector from the cultured transformant, and
    contacting the recovered amide hydrolase with an α-amino acid amide to produce an optically active L-α-amino acid.

19. A process for producing an optically active L-α-amino acid, comprising:
    culturing the microorganism according to claim 11,
    recovering an amide hydrolase from the microorganism, wherein the amide hydrolase is encoded by a polynucleotide comprising the nucleotide sequence of SEQ ID NO:2, and
    contacting the recovered amide hydrolase with an α-amino acid amide to produce an optically active L-α-amino acid.

* * * * *

SEQUENCE LISTING

```
<160> NUMBER OF SEQ ID NOS: 2

<210> SEQ ID NO 1
<211> LENGTH: 309
<212> TYPE: PRT
<213> ORGANISM: Thermus sp.
<220> FEATURE:
<221> NAME/KEY: variant
<222> LOCATION: 1
<223> OTHER INFORMATION: Xaa = Met or absent

<400> SEQUENCE: 1

Xaa Lys Gly Tyr Arg Thr Ile His Arg Glu His His His Phe Gly Trp
 1               5                  10                  15

Asp Asn Gly Leu Pro Pro Val Ala Arg Val Phe Pro Gly Glu Val Val
                20                  25                  30

Glu Phe Glu Val Val Asp Ala Ser Gly Gly Gln Leu Thr Pro Gly Ala
            35                  40                  45

Thr Ala Glu Asp Val Ala Arg Leu Asp Phe Ala Arg Val Asn Pro Val
        50                  55                  60

Thr Gly Pro Val Leu Val Asp Gly Ala Glu Pro Gly Asp Ala Leu Val
    65                  70                  75                  80

Val Glu Val Val Gly Leu Glu Gly Ser Gly Trp Gly Trp Thr Ala Ile
                85                  90                  95

Ile Pro Gly Phe Gly Leu Leu Ala Glu Asp Phe Pro Asn Pro His Leu
                100                 105                 110

His Phe Ser Gln Tyr His Leu Gly Val Glu Phe Leu Pro Gly Val
            115                 120                 125

Arg Leu Pro Tyr Arg Pro Phe Pro Gly Thr Ile Gly Val Ala Pro Ala
        130                 135                 140

Ala Pro Gly Val His Ser Val Pro Pro Arg Glu Val Gly Gly Asn
    145                 150                 155                 160

Leu Asp Ile Arg Asp Leu Val Glu Gly Ala Arg Leu Phe Leu Pro Val
                165                 170                 175
```

Gln Val Pro Gly Ala Leu Phe Ser Val Gly Asp Thr His Ala Val Gln
            180                 185                 190

Gly Asp Gly Glu Val Cys Gly Thr Ala Val Glu Ser Pro Met Arg Ile
        195                 200                 205

Ala Leu Arg Phe Asp Leu Arg Lys Glu Ala Arg Ile Pro Arg Pro Ala
    210                 215                 220

Phe Glu Val Pro Arg Gly Ser Ala Lys Val Pro Gly Glu Arg Gly Phe
225                 230                 235                 240

Phe Ala Thr Thr Gly Ile Ala Pro Asp Leu Met Leu Ala Ala Lys Asp
                245                 250                 255

Ala Val Arg Tyr Met Ile Asp His Leu Gly Arg Glu Tyr Gly Leu Ser
            260                 265                 270

Pro Glu Lys Ala Tyr Met Leu Cys Ser Val Ala Val Asp Leu Arg Ile
        275                 280                 285

Ser Glu Val Val Asp Ala Pro Asn Trp Val Val Ser Ala Tyr Leu Pro
    290                 295                 300

Val Asp Ile Phe Ala
305

<210> SEQ ID NO 2
<211> LENGTH: 930
<212> TYPE: DNA
<213> ORGANISM: Thermus sp.
<300> PUBLICATION INFORMATION:

<400> SEQUENCE: 2

```
atgaagggct acaggaccat tcatcgggag catcaccact tcggctggga taatggactg      60 ccccccggtag ccagggtatt tccgggagag gtggtgaat tcgaggtggt ggacgcctct    120
ggagggcagc tgacgccggg tgccaccgct gaagacgtgg ctcgtctgga cttcgcccgg    180
gtaaacccgg tcacgggtcc cgtgctggtg acggggctg agccggggga tgccctggtg    240
gtggaggtgg tgggcctcga ggggtcgggg tggggctgga cggccatcat ccccgggttt    300
gggctgttgg cggaagactt tccaaatccg cacttgcact tttcgcaata ccacttgggt    360
ggcgtggagt ttctacctgg agtccggcta ccgtacaggc ctttccccgg caccatcggc    420
gtggctcctg cggcccctgg ggtgcactcc gtggttccac cgcgggaggt gggaggcaac    480
ctggacatcc gcgacctggt ggaagggcg agactcttcc ttccggtgca ggtgccgggg    540
gccctgttct ctgtgggcga cacccacgcc gttcaggggg acggcgaggt gtgtggcacc    600
gcagtggagt cacccatgcg gatcgcccta cgttttgacc tgcgcaagga ggccaggata    660
ccgcgcccgg cttttgaagt cccacgcgga tcagcaaaag ttccagggga gagaggcttt    720
tttgccacca cagggattgc tccggacctt atgcttgcgg ccaaggatgc ggtacgctac    780
atgatcgacc acctagggcg ggagtatggg ctatccccgg agaaggcgta catgctctgc    840
agcgtggcag tggacctaag aatcagcgag gtggtggatg cccccaactg ggtggtttcc    900
gcttacctac ccgtggatat tttcgcctga                                       930
```